(12) United States Patent
Nelson et al.

(10) Patent No.: US 10,387,848 B1
(45) Date of Patent: *Aug. 20, 2019

(54) METHOD, APPARATUS AND COMPUTER PROGRAM TO PROVIDE ACCESS TO CLIENT RECORDS AND DATA RESOURCES

(71) Applicant: West Corporation, Omaha, NE (US)

(72) Inventors: Cindy Rae Nelson, Spanish Fort, AL (US); Charles Stephen Fesler, Mobile, AL (US); Theodore Ellzey McGallagher, Mobile, AL (US)

(73) Assignee: West Corporation, Omaha, NE (US)

( * ) Notice: Subject to any disclaimer, the term of this patent is extended or adjusted under 35 U.S.C. 154(b) by 402 days.

This patent is subject to a terminal disclaimer.

(21) Appl. No.: 15/396,887

(22) Filed: Jan. 3, 2017

Related U.S. Application Data

(63) Continuation of application No. 15/145,200, filed on May 3, 2016, now Pat. No. 9,536,048, which is a continuation of application No. 12/758,936, filed on Apr. 13, 2010, now Pat. No. 9,330,234.

(51) Int. Cl.
*G06F 15/16* (2006.01)
*G06Q 10/10* (2012.01)
*G06F 16/25* (2019.01)
*G06F 16/23* (2019.01)

(52) U.S. Cl.
CPC ..... *G06Q 10/1095* (2013.01); *G06F 16/2372* (2019.01); *G06F 16/252* (2019.01)

(58) Field of Classification Search
None
See application file for complete search history.

(56) References Cited

U.S. PATENT DOCUMENTS

| 7,774,391 | B1 * | 8/2010 | Le | G06F 16/13 |
| | | | | 707/822 |
| 8,504,597 | B2 * | 8/2013 | Pitts | H04N 21/222 |
| | | | | 707/827 |
| 9,330,234 | B1 * | 5/2016 | Nelson | G06F 16/183 |
| 9,755,856 | B1 * | 9/2017 | Nelson | G06F 16/242 |
| 10,218,537 | B1 * | 2/2019 | Nelson | G06F 16/242 |
| 2004/0019501 | A1 * | 1/2004 | White | G06Q 10/109 |
| | | | | 705/2 |
| 2005/0027568 | A1 * | 2/2005 | Dorris | G16H 10/60 |
| | | | | 705/3 |
| 2006/0294181 | A1 * | 12/2006 | Barzacanos | H04L 67/24 |
| | | | | 709/203 |

(Continued)

*Primary Examiner* — Dhairya A Patel
(74) *Attorney, Agent, or Firm* — Raffi Gostanian

(57) ABSTRACT

A method, computer program and apparatus are disclosed that include accessing client data records, such as, medical records. The method for may include, for example, receiving a data file at a file server comprising client records information. The method may also include forwarding the file to a database and adding the file to a record in the database, creating a database file and storing the database file on the file server, and scheduling a call to at least one client, the call including a portion of the information included in the received data file. The method may further provide performing the call, monitoring the call, and may also include updating the client records information stored in the database based on the additional information provided by the at least one client.

18 Claims, 4 Drawing Sheets

(56) References Cited

U.S. PATENT DOCUMENTS

| | | | |
|---|---|---|---|
| 2009/0048869 A1* | 2/2009 | Tyler | H04M 11/10 705/2 |
| 2009/0138283 A1* | 5/2009 | Brown | G06Q 10/109 705/3 |
| 2009/0144422 A1* | 6/2009 | Chatley | G06F 3/0613 709/226 |
| 2009/0161846 A1* | 6/2009 | Perrin | G06Q 10/10 379/93.25 |
| 2010/0131630 A1* | 5/2010 | Kondamuru | G06F 9/5083 709/222 |
| 2010/0153487 A1* | 6/2010 | Greven | G06Q 10/06311 709/203 |
| 2010/0268661 A1* | 10/2010 | Levy | G06Q 30/02 705/347 |

* cited by examiner

METHOD, APPARATUS AND COMPUTER PROGRAM TO PROVIDE ACCESS TO CLIENT RECORDS AND DATA RESOURCES

CROSS-REFERENCE TO RELATED APPLICATIONS

This application is a continuation from U.S. patent application Ser. No. 15/145,200, filed May 3, 2016, entitled "METHOD, APPARATUS AND COMPUTER PROGRAM TO PROVIDE ACCESS TO CLIENT RECORDS AND DATA", which is a continuation from U.S. patent application Ser. No. 12/758,936, filed Apr. 13, 2010, entitled "METHOD, APPARATUS AND COMPUTER PROGRAM TO PROVIDE ACCESS TO CLIENT RECORDS AND DATA", now issued U.S. Pat. No. 9,330,234, the entire contents of each of which are incorporated by reference herein in their entirety.

FIELD OF THE INVENTION

The present inventive concept is related to a data records configuration that allows clients to access their personal data records and to receive updated information pertaining to their personal records information.

BACKGROUND OF THE INVENTION

Conventional data record systems that provide client access to their personal records may be provided by a variety of different mediums and networking systems. One example of a data record system may be a telephony-based system which allows clients to access their personal record information by operating a telephone. For instance, a client may wish to access personal medical records stored in a remote database by calling a phone-based data record system and accessing their records via keypad entries or voice commands made over their telephones.

The telephony-based data record systems may provide access to client records through a remote web server and a corresponding database. For example, FIG. 1 illustrates a conventional data record accessing system 10A. Referring to FIG. 1, client 100 uses a hypertext transfer protocol script secure (HTTPS) web posting application to connect to a web server 101 over the network, which is illustrated by the network cloud that may represent a wide area network, the Internet, etc. Once a connection is established the client may send a data file to the web server 101.

The data file is originally sent to the web server 101 which provides a connection to a file server 102. After the file has been moved to the file server 102, a record is generated based on the received file, and that record is sent to a database server, such as, for example, a SQL server 103. The SQL server 103 receives the data file and a record may be generated and added to the SQL database in the SQL server 103.

The file server 102 includes two server engines, which include a parser server engine 102A and an image parser engine 102B. These file server engines provide additional features for processing the data files which are sent to the file server 102. For example, parser server 102A may read and write the data files to the SQL cluster at the SQL server 103. Other applications performed by the file server 102 may include file branding, storing and accessing of appointment file information and voice files (i.e., VCE files).

The SQL sever 103 may also provide additional applications, such as, a parse queue to parse data received from the data file, appointment data organization and storage, email applications for sending reminders to individuals including bulk email, news letter creation and updating procedures, after hours data access services for clients, and short messaging services (SMS) for clients.

The parser server 102A may also parse information for the client, such as, appointment data, and then format the appointment data for storage in appointment tables. The image parser may obtain image information stored in a remote storage unit 104, which may be a database of pre-stored data records, for example, dental records, medical records, x-rays, client chart information, etc.

After data has been stored and processed by the data record accessing system 10A, the clients may access the data records by using an internet portal link to connect to the web server 101 and access client data records. For example, a client may access pre-stored records to obtain appointment information of an approaching doctor appointment based on client data records previously stored in the appointment tables by the file server 102 and the parser server 102A.

Upon accessing the client's records, certain information may be provided automatically or in response to a request submitted by the client accessing the client's records. For instance, images that are stored in the storage 104 and that are associated with the client's personal data may be offered to the client and downloaded to the client's terminal device (not shown).

A similar access scheme may be performed by a client calling in over a telephone to a telephone server 106, which includes an engine 106A and a voice board 106B. For example, after the offices are closed, clients may desire to access their personal data records so that certain information may be confirmed, such as, their appointment time for their next doctor visit.

The engine 106A and the voice board 106B provide the clients with the necessary options to access their personal information. The client may access appointment information and pre-recorded voice file (VCE) information from the file server 102 regarding personal record information. In addition, the telephone server 106 may provide an emergency service that calls the clients when their related personal medical information requires immediate attention. The emergency notifications may also be provided by e-mail, text messaging and other notification techniques via the e-mail server 105.

The conventional data record accessing system 10A performs data record storage and accessing options without anticipating changes to the clients' needs and without providing a dynamic updating platform. Clients need access to all of their personal records, and also need to update their personal records based on the changes that may occur since their last information accessing session and/or during their current sessions with the data record assessing system.

SUMMARY OF THE INVENTION

Disclosed is an optimized method, computer program and apparatus to access data records that allows clients to access their personal data records and to receive updated information pertaining to their personal records information.

One example embodiment of the present inventive concept includes a method or computer program that includes receiving a data file at a file server comprising client records information. The method may also include forwarding the file to a database and adding the file to a record in the database. The method may further include creating a database file and storing the database file on the file server. The method may also include scheduling a call to at least one client, the call including a portion of the information included in the received data file. The method may further provide performing the call to the at least one client, and monitoring the call to determine if any additional information is provided from the at least one client during the course of the call. The method may also include updating the client records information stored in the database based on the additional information provided by the at least one client.

Another example embodiment of the present inventive concept may also include an apparatus that includes a file server configured to access client data records. The file server may include a receiver configured to receive a data file at the file server comprising client records information, and a transmitter configured to transmit the file to a database where the file is added to a record in the database. The file server may also include a processor configured to create a database file and storing the database file on the file server, schedule a call to at least one client, the call including a portion of the information included in the received data file, perform the call to the at least one client, monitor the call to determine if any additional information is provided from the at least one client during the course of the call, and update the client records information stored in the database based on the additional information provided by the at least one client.

DETAILED DESCRIPTION OF THE PREFERRED EMBODIMENTS

Figure 1:
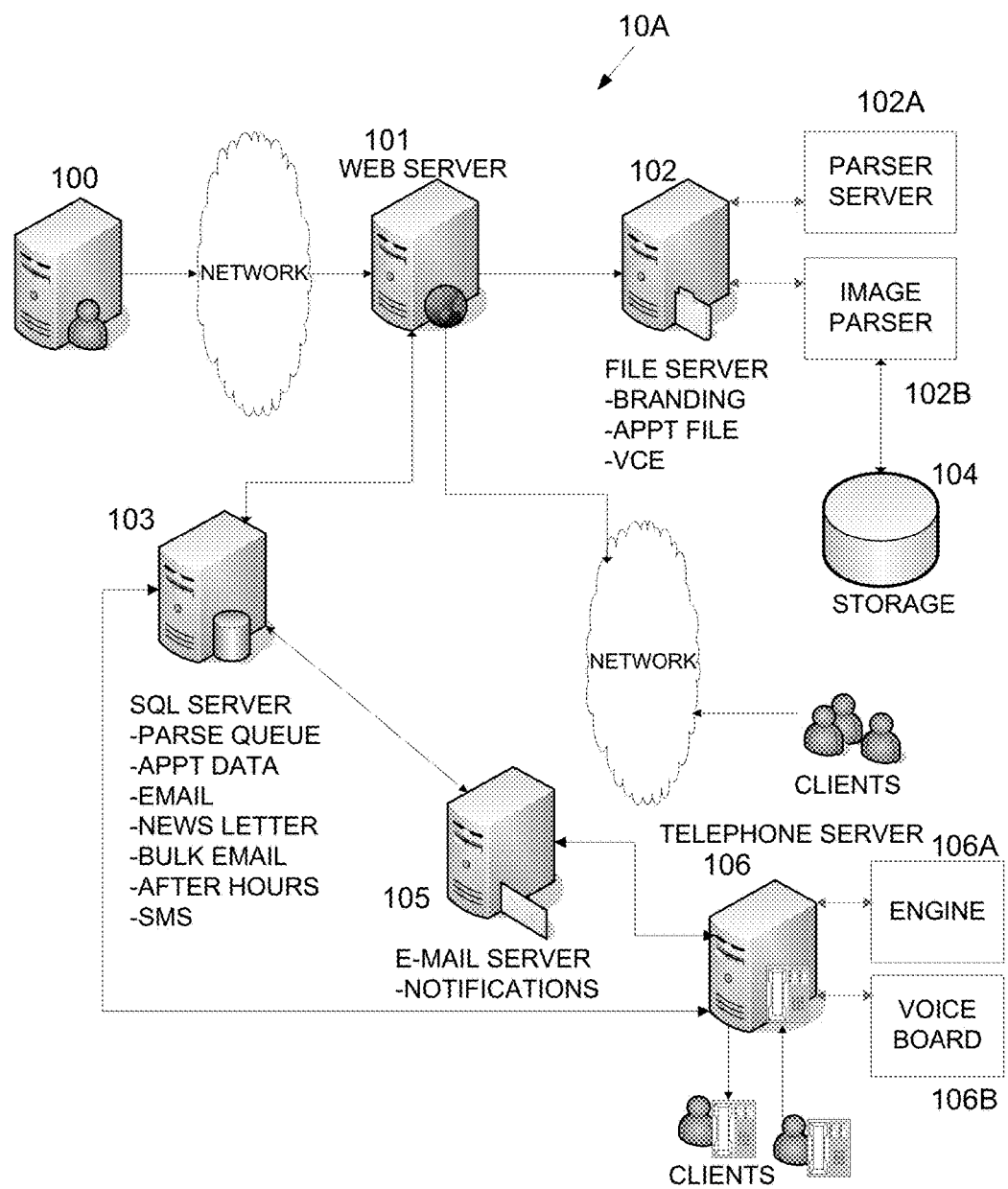
FIG. 1 illustrates a conventional data record accessing system.
Figure 2:
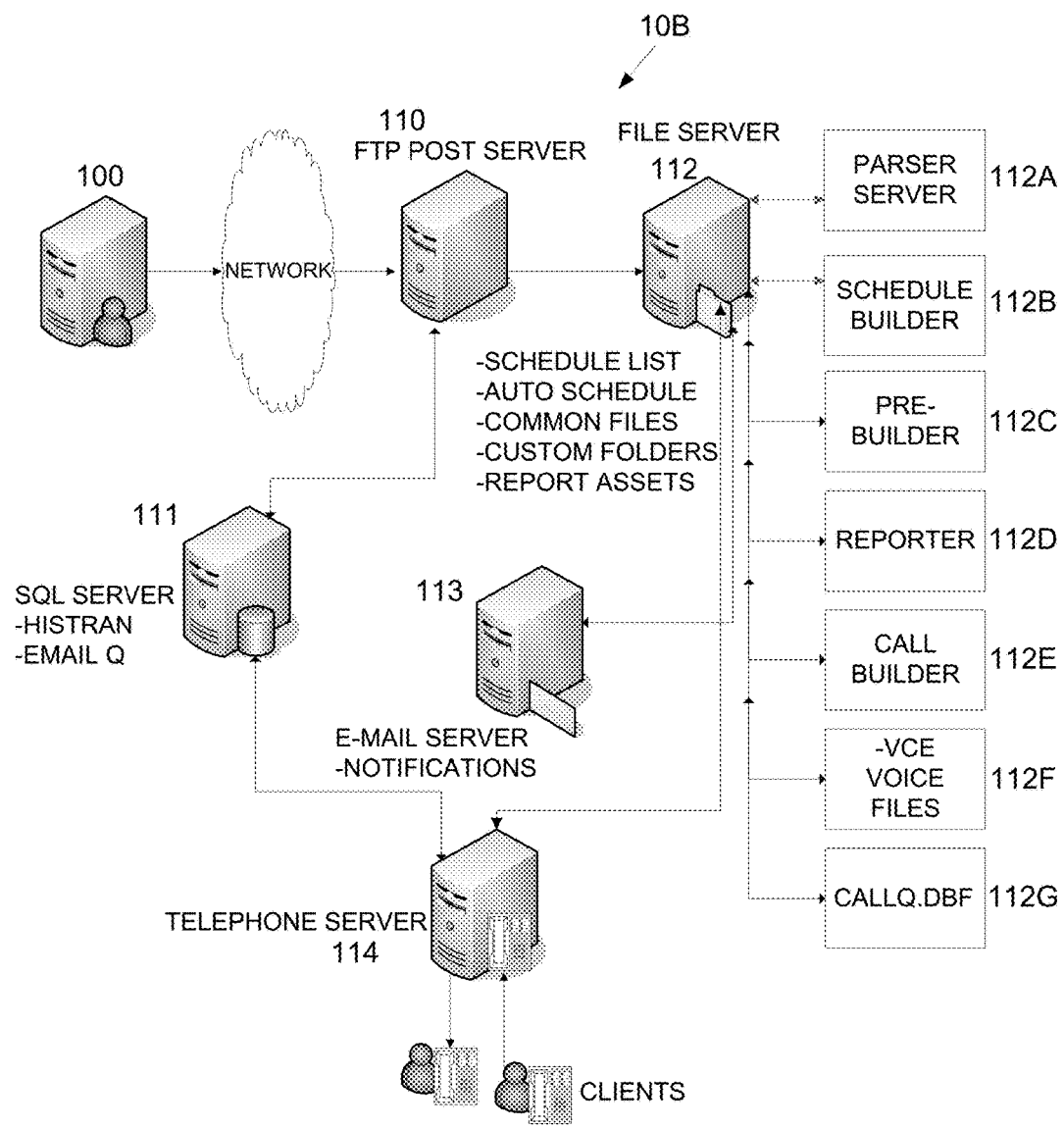
FIG. 2 illustrates an example data record accessing system according to an example embodiment of the present inventive concept.

FIG. 2 illustrates a data record accessing system 10B according to an example embodiment of the present inventive concept. Referring to FIG. 2, client 100 uses a web posting application to connect to a file transfer protocol (FTP) application server 110 over a network illustrated by the network cloud that may represent a wide area network, the Internet, etc. Once a connection is established, the client 100 may send a data file to the FTP post server 110 (which may also include a secure shell (SSH) application).

The data file is originally sent to the FTP post server 110 which provides a connection to a file server 112. After the file has been moved to the file server 112, a record is generated based on the received file, and that record is sent to a database server, such as, for example, a SQL server 113. The SQL server 113 receives the data file and a record may be generated and added to the SQL database in the SQL server 113.

The file server 112 includes multiple server engines, which include a parser server engine 112A, an image parser engine 112B, a pre-builder engine 112C, a reporter engine 112D and a call builder engine 112E. The file server 112 may store VCE voice files and a CallQ.DBF file 112G in its internal memory. Operations performed by file server 112 may include creation and updating of scheduling lists, auto scheduling of client applications and appointments, storing and accessing of common files associated with client information, creating and accessing of custom folders, and reporting of assets to clients.

The file server engines 112A-112E provide additional features for processing the data files which are sent to the file server 112. For example, parser server 112A may read and write the data files to the SQL cluster at the SQL server 113. The parser server 112A may also parse information for the client, such as, appointment data, and then format the appointment data for storage in appointment tables. The schedule builder 112B reviews schedules of clients and builds a record file database file (i.e., CallQ.dbf file 112G).

The pre-builder 112C builds the voice files (VCE files) for the clients' records so that the clients may access their records and listen to the voice files corresponding to their records. The pre-builder 112C also performs a query for the scheduled call information that is setup by the schedule builder 112B. The pre-builder will then create a new file build on the file server 112 for client access and for future updates.

The file server 112 may provide certain applications, such as, automatic scheduling of client appointment times, storing and accessing of common files needed for client resources, creating and updating of custom folders for client resources, etc. The file server 112 may also provide a reporter engine 112E that reports resources to other components of the data accessing system 10B and to the clients. Voice data may be accessed from the VCE voice files 112F and other information may be accessed from the database file CallQ.dbf 112G.

One example operation of the data accessing system 10B is discussed in detail below. Next generation future phone calls are created at the telephone server 117. Each of the telephone server lines will access another database file Schlist.dbf to determine schedule information for clients. The database file Schlist.dbf is also used to associate client information with the future calls and to access the existing file build in the file server 112 and/or create a new file build. Additionally, if data for a future call is not built on an existing file build, then, the call may be built on the file telephone server 117.

The calls may then be made to a corresponding set of pre-established clients informing them of their personal information, schedule information, etc. The telephone server 117 may then initiate the calls to the client telephones or call accessing stations (i.e., mobile stations). Once the calls are dialed out, the calls may be further monitored by the telephone server 117 to track the calls progress. During the calls, the call status may be updated periodically and the call status information may be in the CallQ.dbf file 112G on the file server 112.

The reporter engine 112D will query the schedule lists, discover the schedules that are complete and the corresponding client reports that are ready to be sent to the clients. Other operations of the reporter engine 112D may include inserting the record into the SQL server 113, which may offer a Histran application and an email queue service. The files that are ready to be transferred to clients are placed in an export file in the file server 112. The export files are then sent via FTP, SSH, email, autodial applications, fax or a web posting application to the clients. In one example, the emails may be sent in bulk to the various clients in email notifications sent from the email server 116. The FTP server 110 provides a file transfer protocol application that provides easy access to the clients' records.

Figure 3:
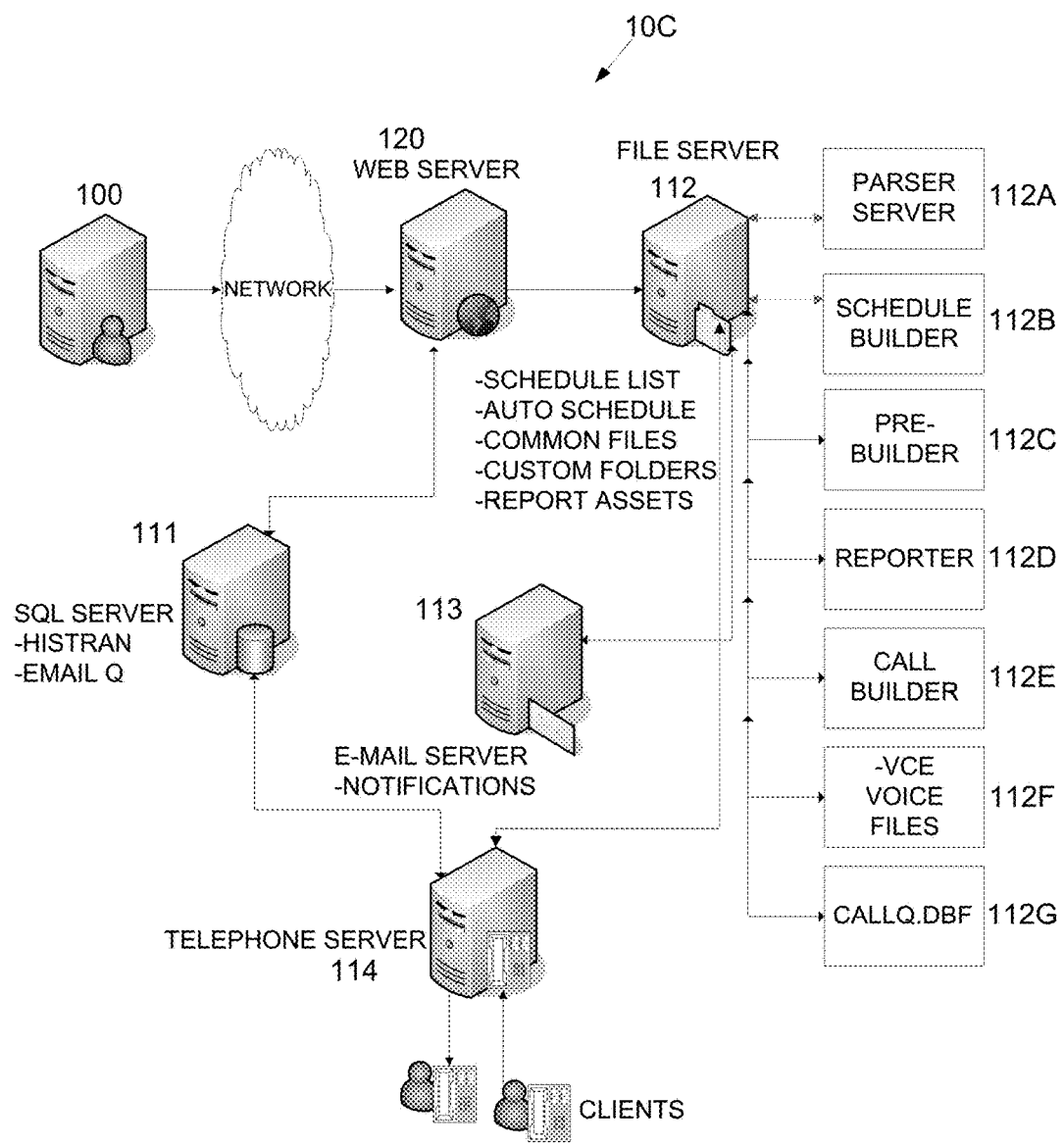
FIG. 3 illustrates another example data record accessing system according to another example embodiment of the present inventive concept.

FIG. 3 illustrates a data record accessing system 10C according to another example embodiment of the present inventive concept. Referring to FIG. 3, client 100 uses a web posting application to connect to web server 120 over a network illustrated by the network cloud that may represent a wide area network, the Internet, etc. Once a connection is established, the client 100 may send a data file to the web server 120.

The data file is originally sent to the web 120 which provides a connection to a file server 112. After the file has been moved to the file server 112, a record is generated based on the received file, and that record is sent to a database server, such as, for example, a SQL server 113. The SQL server 113 receives the data file and a record may be generated and added to the SQL database in the SQL server 113.

The file server 112 includes multiple server engines, which include a parser server engine 112A, an image parser engine 112B, a pre-builder engine 112C, a reporter engine 112D and a call builder engine 112E. The file server 112 may store VCE voice files and a CallQ.DBF file 112G in its internal memory. Operations performed by file server 112 may include creation and updating of scheduling lists, auto scheduling of client applications and appointments, storing and accessing of common files associated with client information, creating and accessing of custom folders, and reporting of assets to clients.

The file server engines 112A-112E provide additional features for processing the data files which are sent to the file server 112. For example, parser server 112A may read and write the data files to the SQL cluster at the SQL server 113. The parser server 112A may also parse information for the client, such as, appointment data, and then format the appointment data for storage in appointment tables. The schedule builder 112B reviews schedules of clients and builds a record file database file (i.e., CallQ.dbf file 112G).

The pre-builder 112C builds the voice files (VCE files) for the clients' records so that the clients may access their records and listen to the voice files corresponding to their records. The pre-builder 112C also performs a query for the scheduled call information that is setup by the schedule builder 112B. The pre-builder will then create a new file build on the file server 112 for client access and for future updates.

In another example, pre-scheduled intervals may be used to perform the various operations of file server 112. For example, the parser server 112A may operate between 12 AM and 3 PM, the schedule builder 112B may operate at mid-day after 3 PM until early evening, and the reporter 112D may finalize and send out reports in the evening so that the clients are reminded of their next-day obligations the evening before their appointments.

The file server 112 may provide certain applications, such as, automatic scheduling of client appointment times, storing and accessing of common files needed for client resources, creating and updating of custom folders for client resources, etc. The file server 112 may also provide a reporter engine 112E that reports resources to other components of the data accessing system 10C and to the clients. Voice data may be accessed from the VCE voice files 112F and other information may be accessed from the database file CallQ.dbf 112G. One or more of these operations may be performed with foxpro and/or other data customization software applications.

One example operation of the data accessing system 10C is discussed in detail below. Next generation future phone calls are created at the telephone server 117. Each of the telephone server lines will access another database file Schlist.dbf to determine schedule information for clients. The database file Schlist.dbf is also used to associate client information with the future calls and to access the existing file build in the file server 112 and/or create a new file build. Additionally, if data for a future call is not built on an existing file build, then, the call may be built on the file telephone server 117.

The calls may then be made to a corresponding set of pre-established clients informing them of their personal information, schedule information, etc. The telephone server 117 may then initiate the calls to the client telephones or call accessing stations (i.e., mobile stations). Once the calls are dialed out, the calls may be further monitored by the telephone server 117 to track the calls progress. During the calls, the call status may be updated periodically and the call status information may be in the CallQ.dbf file 112G on the file server 112.

The reporter engine 112D will query the schedule lists, discover the schedules that are complete and the corresponding client reports that are ready to be sent to the clients. Other operations of the reporter engine 112D may include inserting the record into the SQL server 113, which may offer a Histran application and an email queue service. The files that are ready to be transferred to clients are placed in an export file in the file server 112. The export files are then sent via email, autodial applications, fax or a web posting application to the clients. In one example, the emails may be sent in bulk to the various clients in email notifications sent from the email server 116. The web server 120 provides a web portal application that provides easy access to the clients' records.

Figure 4:
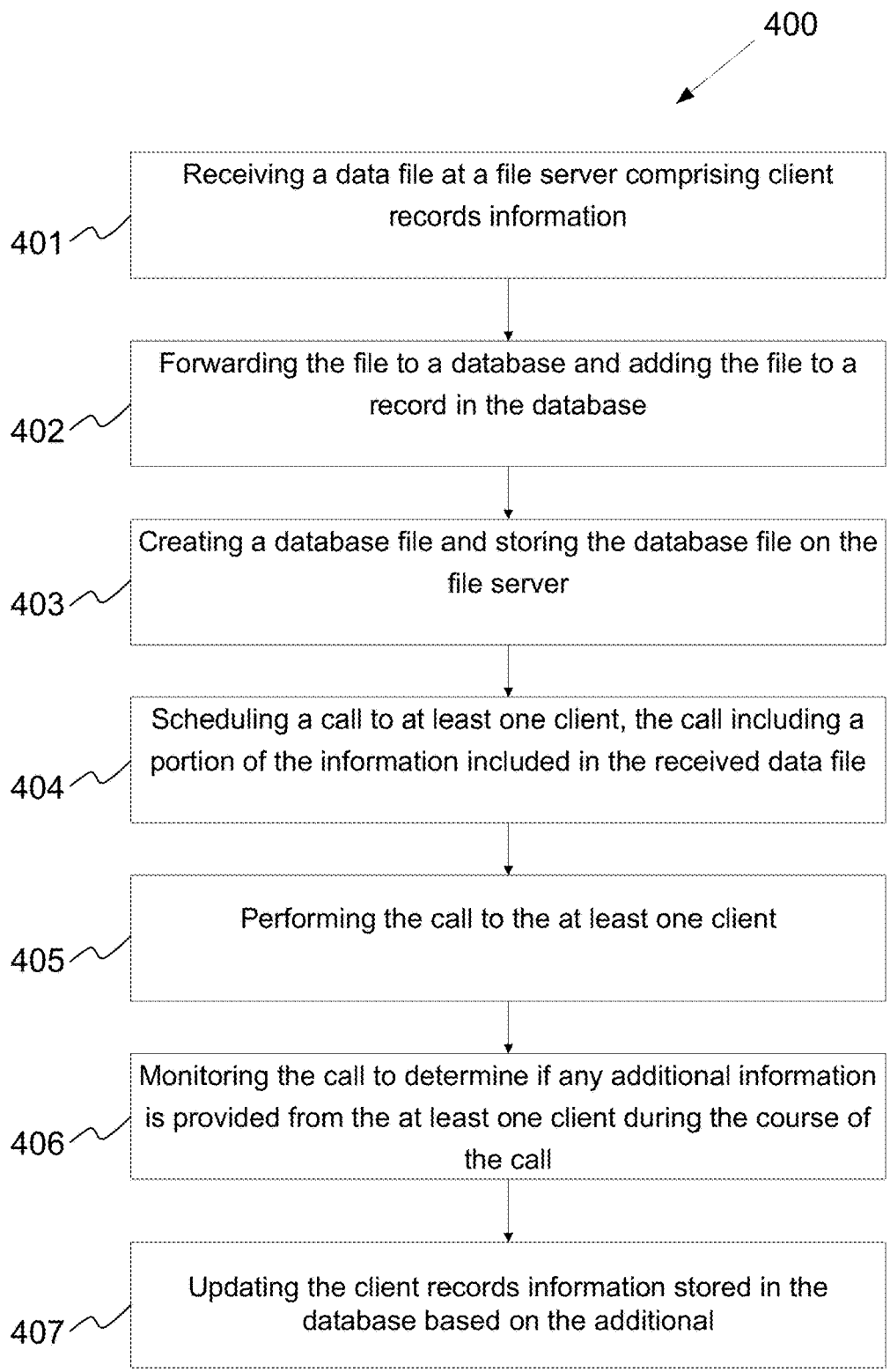
FIG. 4 illustrates a flow diagram according to illustrates an example embodiment of the present inventive concept.

Another example embodiment of the present inventive concept is illustrated in FIG. 4. Referring to FIG. 4, operations of the data file accessing configuration may include receiving a data file at a file server comprising client records information (operation 401). Other operations may include forwarding the file to a database and adding the file to a record in the database, (operation 402), creating a database file and storing the database file on the file server (operation 403), and scheduling a call to at least one client, the call including a portion of the information included in the received data file (operation 404). Further operations may include performing the call to the at least one client (operation 405), monitoring the call to determine if any additional information is provided from the at least one client during the course of the call (operation 406), and updating the client records information stored in the database based on the additional information provided by the at least one client (operation 407).

The present inventive concept is preferably realized in a hardware device, such as, a computer, cellular phone, or other mobile terminal device etc. In other embodiments, the present invention may be realized in hardware, software, firmware or a combination of hardware, software and/or firmware.

The above example embodiments may also be implemented in software code and may be stored on a computer readable medium, such as, for example, non-volatile memory devices (e.g., RAM, ROM, hard disk etc.). The software code may be accessed from the computer readable medium and may be executed by a processor. The executed program may provide one or more of the features of the example embodiments.

While preferred embodiments of the present invention have been described, it is to be understood that the embodiments described are illustrative only and the scope of the invention is to be defined solely by the appended claims when considered with a full range of equivalents and modifications (e.g., protocols, hardware devices, software platforms etc.) thereto.

What is claimed is:

1. A method, comprising:
receiving a data file from a client at a file server comprising client records information of the client;
parsing information for the client including appointment data by a parsing engine, and formatting the appointment data for storage in one or more appointment tables;
scheduling, by a schedule builder, a call to at least one client, the call including a portion of the information of the client included in the received data file, wherein the schedule builder reviews appointment data in the one or more appointment tables and builds one or more schedule lists;
building a voice file using the portion of the information so that the at least one client may access their respective record and listen to the voice file corresponding to their respective record; and
sending the voice file including the portion of the information to the at least one client over the scheduled call, wherein the voice file is sent by a reporter engine;
wherein the parsing engine, schedule builder and reporting engine operate on a daily cycle such the parser engine operates for a first time period during the day, the schedule builder operates for a second time period, and the reporter engine operates for a third time period after the second time period;
wherein an export file on the file server is created based on a list of scheduled information that is determined to be a completed list of the scheduled information by the file server.

2. The method of claim 1, wherein the data file is transferred from the at least one client to at least one of an FTP server and a SSH server prior to said data file being received at the file server.

3. The method of claim 1, wherein the data file is transferred from the at least one client to a web server prior to said data file being received at the file server.

4. The method of claim 1, comprising at least one of:
forwarding the file to a database and adding the file to a record in the database;
creating a database file and storing the database file on the file server; and
updating the client records information stored in the database based on updated client information provided by the at least one client.

5. The method of claim 4, wherein the database is a SQL server database.

6. The method of claim 1, wherein the call is at least one of a dialed call, an email, a text message and a fax.

7. The method of claim 1, wherein the call is transferred via at least one FTP and SSH.

8. A non-transitory computer readable medium storing a software program that when executed controls a processor to perform:
receiving a data file from a client at a file server comprising client records information;
parsing information for the client including appointment data and formatting the appointment data for storage in one or more appointment tables;
scheduling a call to at least one client, the call including a portion of the information of the client included in the received data file, wherein the scheduling comprises reviewing appointment data in the one or more appointment tables and building one or more schedule lists;
building a voice file using the portion of the information so that the at least one client may access their respective record and listen to the voice file corresponding to their respective record; and
sending the voice file including the portion of the information the voice file to the at least one client over the scheduled call, wherein the voice file is sent by a reporter engine;
wherein the parsing, scheduling and reporting engine operate on a daily cycle such the parsing operates for a first time period during the day, the scheduling operates for a second time period, and the reporter engine operates for a third time period after the second time period;
wherein an export file on the file server is created based on a list of scheduled information that is determined to be a completed list of the scheduled information by the file server.

9. The non-transitory computer readable medium of claim 8, wherein the data file is transferred from the at least one client to at least one of an FTP server and a SSH server prior to said data file being received at the file server.

10. The non-transitory computer readable medium of claim 8, wherein the data file is transferred from the at least one client to a web server prior to said data file being received at the file server.

11. The non-transitory computer readable medium of claim 8, wherein the processor is further configured to perform:
forwarding the file to a database and adding the file to a record in the database;
creating a database file and storing the database file on the file server; and
updating the client records information stored in the database based on updated client information provided by the at least one client.

12. The non-transitory computer readable medium of claim 11, wherein the database is a SQL server database.

13. The non-transitory computer readable medium of claim 8, wherein the call is at least one of a dialed call, an email, a text message and a fax.

14. The non-transitory computer readable medium of claim 8, wherein the call is transferred via at least one FTP and SSH.

15. A server, comprising:
a receiver configured to receive a data file from a client at the file server comprising client records information; and
a processor configured to parse information for the client including appointment data and format the appointment data for storage in one or more appointment tables, schedule a call to at least one client, the call including a portion of the information of the client included in the received data file wherein the scheduling comprises reviewing appointment data in the one or more appointment tables and building one or more schedule lists, build a voice file using the portion of the information so that the at least one client may access their respective record and listen to the voice file corresponding to their respective record, send the voice file including the portion of the information to the at least one client over the scheduled call wherein the voice file is sent by a reporter engine, wherein the parsing, scheduling and reporting engine operate on a daily cycle such the parsing operates for a first time period during the day, the scheduling operates for a second time period, and the reporter engine operates for a third time period after the second time period;

wherein an export file on the file server is created based on a list of scheduled information that is determined to be a completed list of the scheduled information by the file server.

16. The file server of claim 15, wherein the data file is transferred from the at least one client to at least one of an FTP server and a SSH server prior to said data file being received at the file server.

17. The file server of claim 15, wherein the data file is transferred from the at least one client to a web server prior to said data file being received at the file server.

18. The file server of claim 15, wherein the call is transferred via at least one FTP and SSH.

* * * * *